United States Patent [19]

Daniel, Jr.

[11] Patent Number: 5,428,660
[45] Date of Patent: Jun. 27, 1995

[54] PORTABLE MEDICAL PANORAMIC RADIOGRAPHIC DEVICE

[75] Inventor: Charles R. Daniel, Jr., Charleston, S.C.

[73] Assignee: Medical University of South Carolina, Charleston, S.C.

[21] Appl. No.: 154,978

[22] Filed: Nov. 19, 1993

[51] Int. Cl.6 .............................................. H05G 1/02
[52] U.S. Cl. .................................... 378/197; 378/198; 378/167; 378/181
[58] Field of Search ...................... 378/38, 39, 40, 167, 378/168, 174, 175, 181, 193, 194, 195, 196, 197, 198

[56] References Cited

U.S. PATENT DOCUMENTS

| | | | |
|---|---|---|---|
| 2,798,958 | 7/1957 | Hudson et al. | 378/39 |
| 2,939,008 | 5/1960 | Goodfriend | 378/181 |
| 3,617,742 | 11/1971 | Schulman | 378/38 |
| 4,034,225 | 7/1977 | Hudson et al. | 250/471 |
| 4,172,977 | 10/1979 | Ciavatonni et al. | 250/439 |
| 4,198,566 | 4/1980 | Nieminen | 250/439 |
| 4,247,779 | 1/1981 | Ciavattoni et al. | 250/439 |
| 4,340,971 | 7/1982 | Furuichi et al. | 378/40 |
| 4,365,340 | 12/1982 | Nishikawa et al. | 378/39 |
| 4,599,739 | 7/1986 | Nishikawa et al. | 378/39 |
| 4,641,331 | 2/1987 | Makino et al. | 378/108 |
| 4,955,042 | 9/1990 | Nishikawa | 378/39 |
| 5,012,501 | 4/1991 | Palonen et al. | 378/38 |
| 5,016,264 | 5/1991 | Hyttinen | 378/38 |
| 5,033,070 | 7/1991 | Kanerva et al. | 378/39 |
| 5,058,147 | 10/1991 | Nishikawa et al. | 378/38 |
| 5,093,852 | 3/1992 | Nishikawa et al. | 378/39 |
| 5,199,060 | 3/1993 | Kato | 378/196 |

OTHER PUBLICATIONS

Philips Oralix 70, Documentation No. 4535 983 00488 (Jan. 1987), 4 pages.

Primary Examiner—David P. Porta
Assistant Examiner—Don Wong
Attorney, Agent, or Firm—Needle & Rosenberg

[57] ABSTRACT

A portable, lightweight medical radiographic device having an articulated support is described. The device includes a base, an elongated supporting structure having multiple sections interconnected by adjustable joints, a mount for a radiological camera, and a support for a film cartridge. The camera mount includes a concave, motorized track; the film cartridge support is also concave and may also provide motorized film advancement. A selected human body part to be imaged may be placed between the camera mount and the film track. When the camera, motorized track, and film support are energized, coordinated movement of the camera relative to the film results in a panoramic image of the body part on the exposed film.

15 Claims, 4 Drawing Sheets

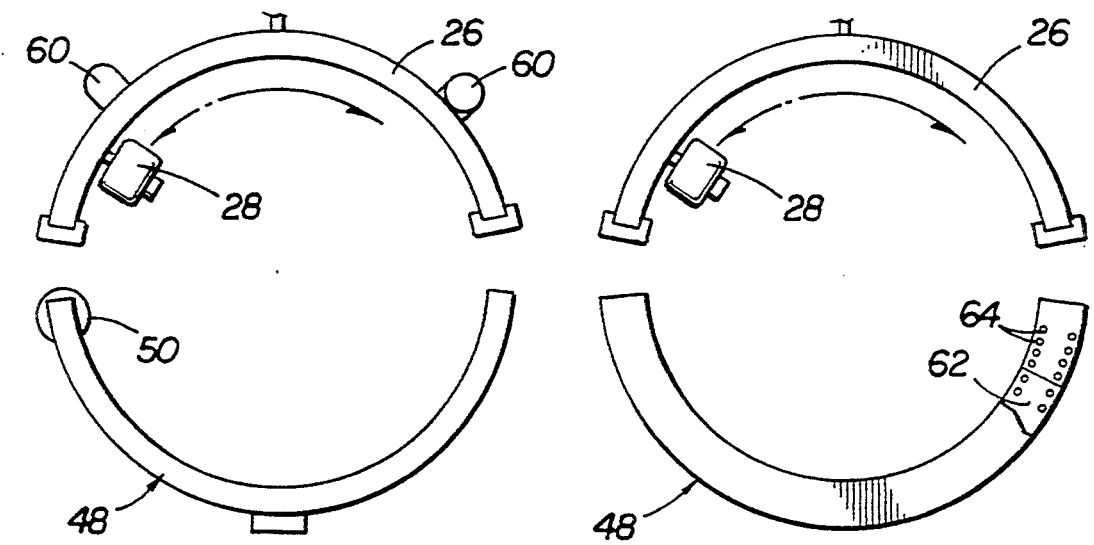
FIG 3A     FIG 3B
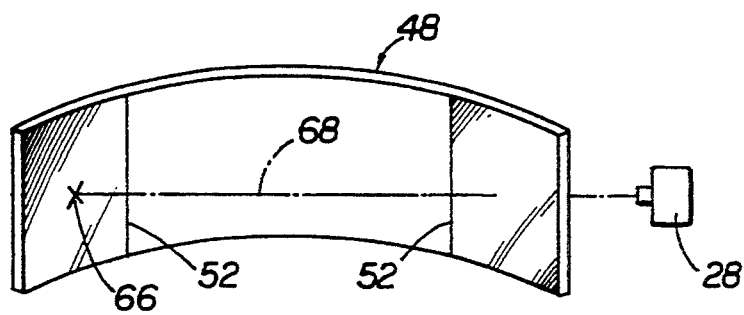
FIG 4
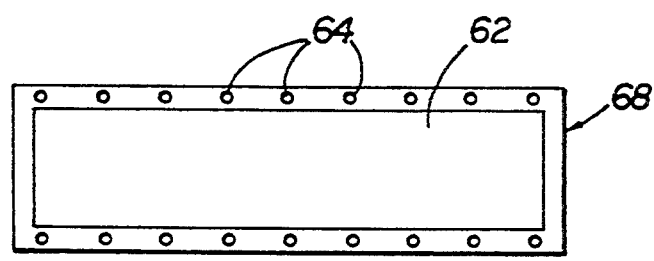
FIG 5

PORTABLE MEDICAL PANORAMIC RADIOGRAPHIC DEVICE

BACKGROUND OF THE INVENTION

1. Field of the Invention

This invention relates to a mobile radiographic unit, and more particularly to a mobile, light-weight, panoramic radiographic unit on which X-rays of a patient may be taken while the patient is in a reclining position or in any non-upright and non-vertical position.

2. Description of the Prior Art

X-ray machines for medical use are commonplace. Perhaps the most familiar of these are those found in a dentist's office. When X-rays are taken with these devices, a patient is typically seated in a specially designed chair, which, although itself adjustable, is fixed to the floor. X-ray film is placed in a carrier, and the carrier and film are placed in the patient's mouth adjacent to the dental area to be radiologically imaged. An X-ray unit on a hinged, or possibly gooseneck-like support, is then placed into the proper position and energized by the dentist or an assistant, exposing the film in the mouth of the patient. This process is typically repeated several times, at least once for each dental region for which an image is required. Panaromic views of the mouth are either highly impractical or impossible with such X-ray devices. Moreover, the chair and X-ray unit are not portable; the patient must come to the dentist's office and be seated in a particular location to have X-rays taken this way.

Most other medical X-rays, such as those in physician's offices and hospitals are also taken with devices that are non-portable. Generally, a patient must either go under his own power to a place where the X-ray can be taken, or he must be carried there. Even if the patient is carried to the X-ray machine because he is otherwise non-ambulatory, he must usually be removed from a wheelchair, cot or gurney on which he was carried and placed on a special support in an upright/vertical position to have his X-ray taken.

It would thus be desirable from a medical standpoint to have a portable X-ray unit that did not require a patient to be removed from his surgical bed, gurney, table or stretcher. Moreover, it would be very desirable to have an X-ray machine that was capable of producing a panoramic X-ray view, for dental and other purposes.

Portable X-ray units are known to the art, as are mobile stands. One such mobile stand currently marketed comprises a number components that can be assembled and dissasembled readily. In this design, a number of telescoping tubes can be fit together, and the assembled tubes are vertically positioned in a base having four legs and casters to provide a vertical support column. One end of the arm is adapted to hold an X-ray unit, while the other end is adapted to clamp onto the vertical support column at a selected height. The arm holds the X-ray unit at an elevated position horizontally distant from the vertical support column. The X-ray unit may have substantial weight. Since it is held horizontally distant from the vertical support column, the base is designed to accommodate the horizontally-shifted center of gravity, and thus provide a stable support. However, no support is provided for a reclining patient. Also, no means is provided for taking a panoramic X-ray view from such a portable X-ray unit in conjunction with a mobile stand and no means is provided for taking a panoramic x-ray from any position other than the patient being in an upright/vertical position.

SUMMARY OF THE INVENTION

In accordance with one aspect of the invention, there is provided a portable medical radiographic device 8 comprising an articulated support having, at one end, support legs, and at the other end, a motorized film cylinder having an arcuate shape. A moveable radiological source is provided on an adjustable, arcuate track, so that a portion of the patient's body (e.g., his mouth and/or articulated joints or limbs) may be placed between the radiological source and the film cylinder. The track for the radiological source and the film cylinder are adapted so that they may be placed in an opposing relationship, with the portion of the patient's body between them. The radiological source is then moved along its track to direct its radiation through the patient's body, exposing essentially the entire length (or at least a substantial portion thereof) of the film in the film cylinder to produce a panoramic view of the portion of the patient's body.

Optionally, for dental X-rays and other head X-rays, a head positioner is provided. The head positioner comprises a wedge-shaped base, which provides support for and elevates the patient's shoulder, a head support, and an extension arm connecting the head support to the base, so that the head can be slightly elevated to rest comfortably above the shoulder.

BRIEF DESCRIPTION OF THE DIAGRAMS

FIG. 3(a) is a top view of the mounting means for the radiographic source and for the film;

FIG. 3 (b) is a top schematic view of the direction of movement of the film and the radiographic source in FIG. 3 (a);

FIG. 4 is a schematic view of a film cylinder of a preferred embodiment conjunction with an opposing radiographic source;

FIG. 5 is a top view of a film cartridge suitable for use in the film cylinder of embodiment of FIG. 4;

DETAILED DESCRIPTION OF THE INVENTION

Figures 1, 2:
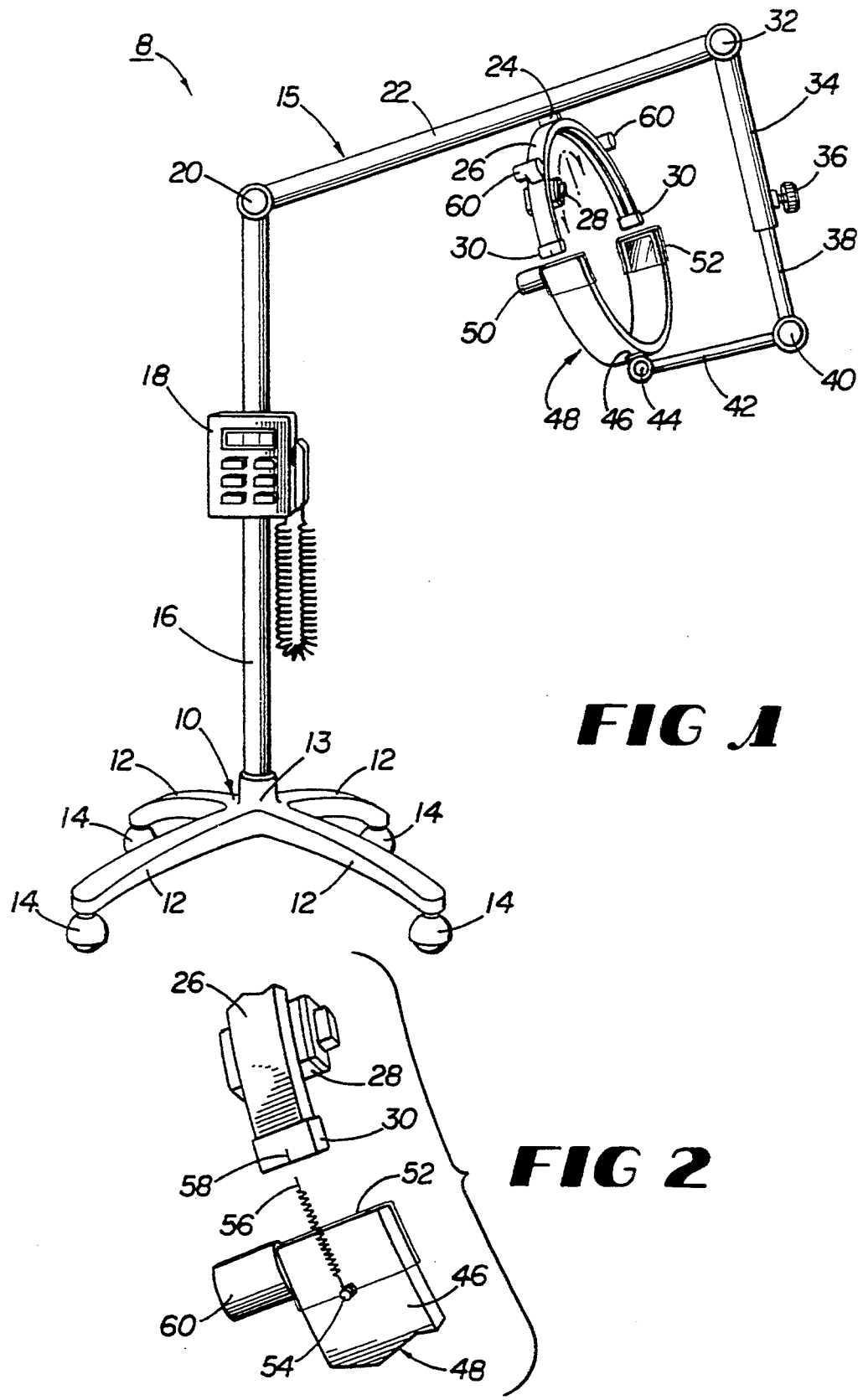
FIG. 1 is a perspective view of a portable panoramic radiographic device in accordance with the invention.
FIG. 2 shows a simple alignment device to line up the film with the radiographic source for proper positioning.

A preferred embodiment of the invention is illustrated in FIG. 1. In this embodiment, which is primarily designed for dental use, the portable radiographic imaging device 8 comprises a base 10, which includes a number of legs 12, 12' radiating as spokes from a hub 13. Casters 14 are provided at the ends of legs 12 and 12' to allow convenient movement of the portable radiographic imaging device 8. As will be further described below, the portion of the portable radiographic imaging device 8 above base 10 has a center of gravity that will not, in general, coincide with hub 13. Therefore, one pair of adjacent legs 12 is larger than the other pair of adjacent legs 12' in the preferred embodiment. It will, of course, be readily appreciated that the details of the base 10 are not critical to the invention; alternate base designs that provide mobility and stability for an off-center and possibly shifting center of gravity can be used.

An elongated, articulated supporting structure 15 having a first support column section 16 is attached at a first end in a conventional manner to the base 10 and rises generally perpendicularly from it. Column section 16 may be made of metal (preferably, a light-weight metal) or any other suitable material. Mounted on column section 16 at a convenient height for the operator of the apparatus is control apparatus 18 for the radiographic source 30 (which is commonly called a "camera," even though the film collecting the image is external to the device), film feed motor 50, and camera tracking motors 60, which are mounted on section 22, as noted below. Although it is not required to be, column section 16 is preferably hollow, which serves not only to reduce its weight, but also to allow wires (not shown) from control apparatus 18 to the electrical components of the imaging device 8 to be run therethrough. Alternately, the wires from control apparatus 18 may simply be run along the outside of the column sections 16, 22.

The second end of first support column section 16 joins with the first end of the second support column section 22 by means of a first joint 20. Joint 20 may preferably be a conventional fully-adjustable positioning joint, or it may simply be a conventional rotatable hinge. Other alternatives are possible, provided that the angle at which second support column section 22 joins first support column section 16 is adjustable. It is also desirable that joint 20 be provided with a positive locking mechanism to prevent slippage once it is appropriately adjusted rather than to rely solely on friction. As with section 16, column section 22 is preferably hollow to reduce the weight of the device and to permit the wires (not shown) to be run therethrough. Certain types of joints 20 also permit wires to run therethrough, for example, hinged joints, and may be used to avoid the necessity of having relatively unprotected wires running along the outside of the device.

Attached to second column section 22 is an adjustable hook 24, which is slidably attached along the length of second column section 22, and which preferably is provided with conventional means to lock the hook 24 at a selectable position along the length of second column section 22. An arcuate or C-shaped motorized track 26 is provided which is attached to hook 24. One or more motors 60 are provided to move a radiological source (camera) 28 along track 26. Power and control for the motors 60 and camera 28 are provided via the power and control wires (not shown) connected to control apparatus 18. Hook 24 may include position adjustments similar to those of a conventional camera tripod base to permit adjustment of the plane in which track 26 is positioned. In addition, track 26 is preferably slidably engaged with hook 24 to allow adjustment of the orientation of track 26 within a selected plane. Track 26 is preferably provided with endpieces 30 to prevent the track from being accidently removed from hook 24 during adjustment and to provide positive stops at the ends of travel of camera 28.

The second end of second column section 22 is attached to a second joint 32, which may be of similar construction to first joint 20. Also attached to second joint 32 is an extension sleeve 34, which slidably engages therein one end of a third column section 38. The slidable engagement of sleeve 34 and column section 38 forms an adjustable length section, allowing the distance between motorized track 26 and film cylinder 48 to be adjusted to better accommodate a portion of a patient's body therebetween. In a preferred embodiment, a tightening nut 36 is provided to lock the third column section 38 in a fixed position within the extension sleeve 34. It will, of course, be understood that other telescoping arrangements may be used, and other locking arrangements are possible.

The other end of third column section 38 is attached to a first end of a fourth column section 42 by means of a third joint 40, which is of a construction similar to joints 32 and 20. The second end of fourth column section 42 is provided, in the preferred embodiment, with a pivot 44, which allows rotation of a leg 46 in one plane. If additional movements are required, however, pivot 44 may be replaced with another type of joint. Leg 46 is attached to the center of a film cylinder 48, into which a film cartridge (not shown in FIG. 1) is placed. Arcuate or C-shaped film cylinder 48 is preferably constructed out of a hollow piece of polymer or a light-weight metal in a manner to be described below. A motor 50 is preferably provided for advancing film in the film cartridge. The motor 50 is powered and controlled by additional power and control wires (not shown) from control apparatus 18, which may preferably be run inside hollow column sections 16, 22, 38, and 42, or alternately, alongside them. Only the back of film cylinder 48 (i.e., the convex side) need be opaque, since X-rays or other radiation from camera 28 will go through the film, which is supported by the concave side of film cylinder 48, the exception being if synchronized, moveable opaque surfaces at certain times need be incorporated along the front of the film to prevent additional overexposure or scattering of the x-ray beam to the yet unexposed film along its path of movement. Film cylinder 48 may be provided with slip-on radiolucent sleeves (not shown) to aid in holding or guiding a film cartridge.

To ensure that, in use, the camera track 26 is positioned so that the camera will expose the entire length of a film cartridge supported in film cylinder 48 and that the beam from the camera will be perpendicular thereto, the ends of film cylinder 48 may be provided with retractable markers 56, as shown in FIG. 2. Marker 56, which is similar to a lanyard, a plumb line, or perhaps a coiled telephone cord, is manually drawn from an attachment point 54 on the film cylinder 48 to an index mark 58 on a camera stop 30 to permit simple visual alignment. Similar alignment markers 56 may be employed at each end of the film cylinder 48 to ensure adequate alignment. Other alignment devices and methods may be used, but the device and method described here has the advantage of being simple and very inexpensive.

Turning now to FIG. 3(a), the tracking of the camera and the film can be readily understood. C-shaped motorized track 26, on which camera 28 travels, is adjusted to permit the camera 28 to be aimed at an opposing section of film cylinder 48 over its entire length of travel along motorized track 26. Adjustment of the apparatus is accomplished by the manipulation of joints 20, 32, 40, and hinge 44, together with the sliding adjustment of motorized track 26 through hook 24 and tilting of hook 24, which is preferably adjustable in several directions as is a camera tripod. One or more motors 60 are provided to move the motor by any conventional means (e.g., sprockets, belts or pulleys) across C-shaped motorized track 26. Motors 60 are also conventional; servo or synchronous motors or any other type suitable for use with an automated camera 28 may be used. An additional motor 50 is for film cylinder 48. (The motor 50 may be mounted in a convenient position along the film cylinder 48.) Of course, the portion of the patient's body to be filmed is placed between the motorized track 26 and the film cylinder 48, so that radiation from camera 28 will pass through the body and expose film in film cylinder 48.

Motor 50 is optional, because film in film cylinder 48 need not be moved during exposure. However, some scattering of the radiation beam will usually occur during exposure, which may overexpose some portions of the film. In addition, it is usually desirable to have an expanded view of the area of the body (such as the teeth and mouth area for dental purposes) provided on the film. Motor 50 provides a solution to the scattering problem as well as providing the desired expanded panoramic view. As shown in FIG. 3(b), during exposure, motor 50 transports film 62 using conventional sprocket holes 64 through film cylinder 48 in the direction of arrow A. Meanwhile, motors 60 transport camera 28 simultaneously over track 26 in the direction shown by arrow B.

It will be readily appreciated that the relative motions of film 62 and camera 28 will spread out not only the image of the body area on the film 62, but will also avoid the scattering problem by spreading out the scattered radiation. The relative speeds of film 62 and camera 28 may be adjusted to control the exposure and degree of image-spreading. It will also be appreciated that a film cartridge containing film 62 must be of greater length than film cylinder 48 if film 62 is moved as shown in FIG. 3(b) and the maximum panoramic view is required. Thus, for a maximum panoramic view, a film cartridge mounted into film cylinder 48 would extend beyond at least one end of film cylinder 48. After exposure, the excess length of the film cartridge will be transferred to the other end of film cylinder 48. The excess film will, at the beginning and end of the exposure, be at the end of the film cylinder 48 adjacent the initial and final positions, respectively, of the camera 28 on motorized track 26.

FIG. 4 shows the relationship of the camera 28 to the film cylinder 48 as might be the case at the beginning of an exposure. Camera 28 projects a beam 68, which travels through a portion of the patient's body (not shown) and onto a spot 66 of the film. Slip-on radiolucent sleeves 52 at either end of film cylinder 48 may be used to guide the film over the film cylinder 48. Other conventional film-guiding means may also be used. Sprockets (not shown) at each end coupled to motor 50 may be used to engage the film so that a spread-out panoramic view is obtained; other means for engaging the film, such as friction rollers, may also be used. A typical film cartridge is shown in FIG. 5, showing sprocket holes 64 for engaging the film 62 with the feeding mechanism of film cylinder 48. The film 62 itself is protected from exposure by film cartridge or sleeve 68 in a manner familiar to those using X-ray films.

A typical use of the device 8 described above is shown in FIG. 6. Patient 70, here shown reclining on a moveable table 74 having legs 76 with casters 78, has his shoulders supported by a shoulder support 72, described in greater detail below. As shown, patient 70 is positioned to provide a panoramic view of the patient's mouth.

Figure 7:
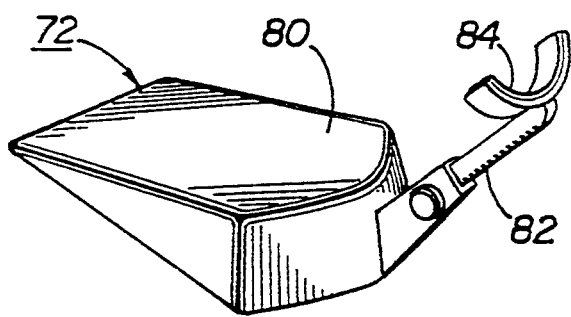
FIG. 7 is a perspective view of a head positioner in accordance with the invention suitable for use with the portable panoramic radiographic device of FIG. 1.

Head positioner 72 is shown in greater detail in FIG. 7. A wedge portion 80 is provided for support under a patient's shoulders. A head support 84 is attached to wedge 80 by a suitable, adjustable extension 82. The positioner 72 is designed to have a stable base with an edge at the shoulder, which is evident in wedge 80 as shown. The shoulders are slightly elevated, and the head rests in a position slightly above the shoulders.

Figure 6:
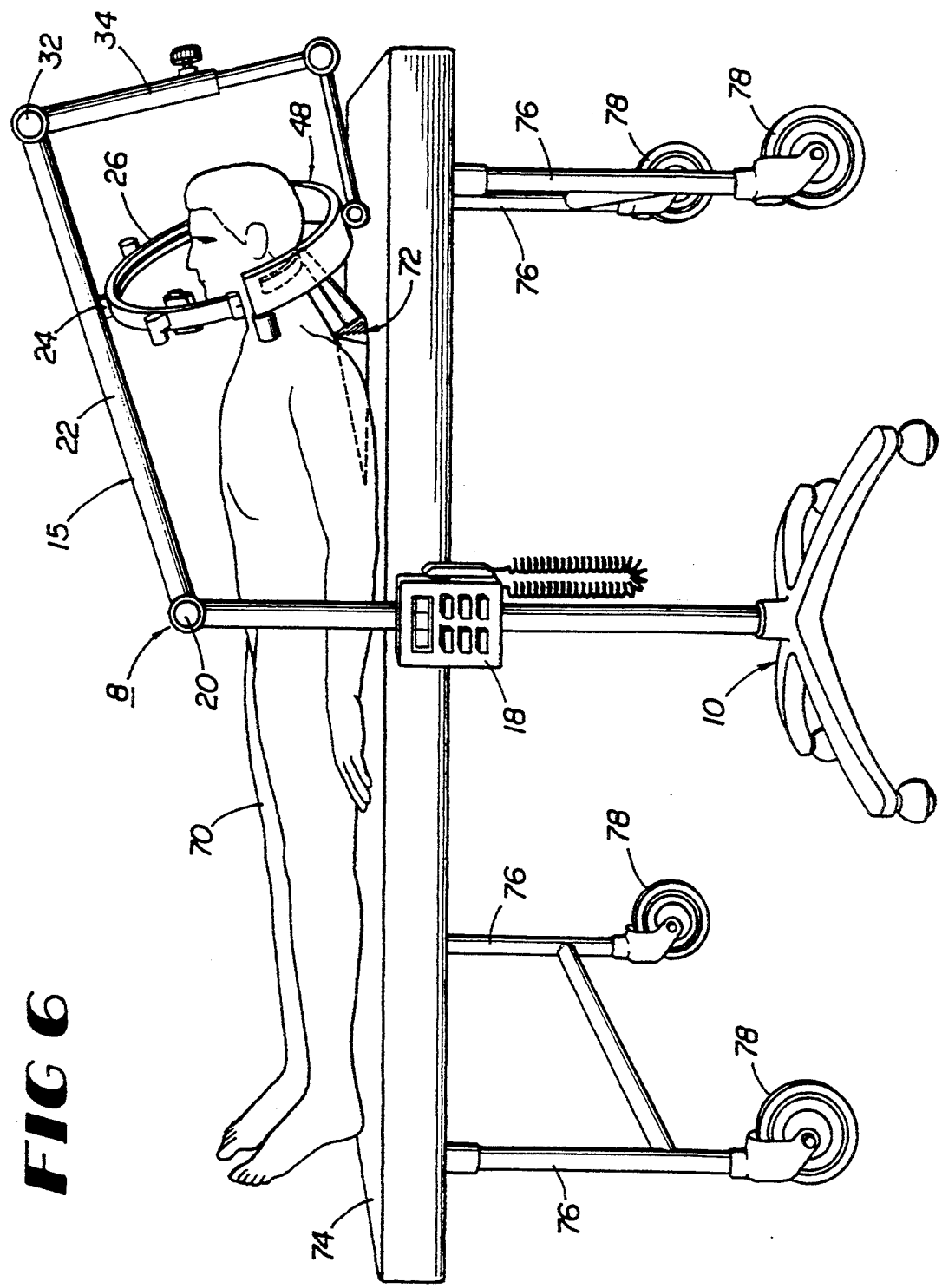
FIG. 6 is a perspective view of the portable panoramic radiographic device in use.

As shown in FIG. 6, the radiographic imaging device 8 is suitable for dental imaging. However, it will be readily apparent that the portable radiographic imaging device 8 may also be used as a radiographic adjunct for OMFS, plastic surgery, ENT, trauma, orthopedic surgery, and other uses where a lightweight, portable imaging device is desirable. It is particularly suitable for non-ambulatory patients, and may be advantageously used in OR (e.g., prior to or post-surgical uses, or swelling/bandaging), in the recovery room, in nursing homes, and in trauma centers.

Figure 8:
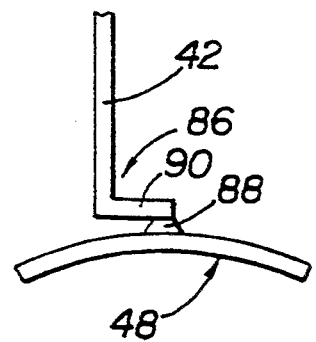
FIG. 8 is a top view of an alternate embodiment of a film cartridge arm suitable for use for radiographic imaging of an elbow or joint.

An alternate embodiment shown in FIG. 8 provides for additional uses of imaging device 8. Here, in a plane perpendicular to the axis of support column 42, film cylinder 48 is fixedly mounted by a mounting means 88 so that the center of the concave portion of the C-shaped cylinder 48 is offset somewhat from the axis of support column 42, such that a line drawn from the axis to the center of the concave portion of C-shaped cylinder 48 in this plane is not perpendicular to a tangent to C-shaped cylinder 48 drawn from this center point. This mounting is more suitable for orthopedic panoramic views of knees, ankles, and elbows, as well as radiolucent cervical collars.

What is claimed is:

1. A portable medical radiographic device for a radiological camera and radiologically sensitive film comprising:

(a) a mobile base;
    (b) an elongate supporting structure attached to the mobile base and the supporting structure comprising a plurality of sections and adjustable joints interconnecting the sections;
    (c) means for mounting the radiological camera at a selected position on a first one of the plurality of sections, the means for mounting comprising an elongated arcuate track for movably mounting the radiological camera on a concave portion thereof, so that rays from the radiological camera are directed away from the concave portion of the track;
    (d) means for supporting the radiologically sensitive film at a selected position on a second one of the plurality of sections, the means for supporting comprising an elongated arcuate cylinder for supporting a film cartridge containing the radiologically sensitive film in a concave portion thereof, so that the radiologically sensitive film is exposed by radiation directed towards the concave portion of the cylinder; and
    (e) energizable camera transport means for moving the radiological camera along the length of the elongated track;

the track and cylinder having adjustable orientations and the first and second ones of the plurality of sections being selected to permit the respective concave portions of the track and the cylinder to be positioned in opposition to one another so that, when a selected portion of a body is interposed between the camera mounting means and the film support means, and the radiological camera and the camera transport means are simultaneously energized, the moving radiological camera exposes an elongate strip of the radiologically sensitive film through the selected portion of the body, thereby creating a panoramic radiological image of the selected portion of the body.

2. The device of claim 1, further comprising energizable film advancement means to transport the radiological film along the length of the cylinder to spread out the radiological image of the selected portion of the body.

3. The device of claim 1, wherein the supporting structure further comprises a third section having an adjustable length, the third section being located between the first and second sections so that the distance between the track and the cylinder is adjustable.

4. The device of claim 3, wherein the third section comprises at least a pair of tubes in slidable engagement with one another.

5. The device of claim 4, wherein the third section comprises a first locking means for locking the pair of tubes in a selected fixed position.

6. The device of claim 1, wherein at least one of the joints is a fully-adjustable positioning joint.

7. The device of claim 1, wherein at least one of the joints is a rotatable hinge.

8. The device of claim 1, wherein at least one of the plurality of sections of the supporting structure is adapted to permit electrical wiring to run therethrough.

9. The device of claim 1, wherein at least a pair of the plurality of sections of the supporting structure and the one of the adjustable joints interconnecting the pair of sections are adapted to permit electrical wiring to run continuously therethrough.

10. The device of claim 1, wherein the camera transport means comprises a servo motor.

11. The device of claim 2, wherein the camera transport means comprises at least a first servo motor, and the film advancement means comprises at least a second servo motor.

12. The device of claim 1, further comprising alignment indicator means for indicating alignment of the track and cylinder.

13. The device of claim 1, further comprising an orientation adjustment means slidably engaged with the track for adjusting the orientation of the track within a selected plane.

14. The device of claim 1, wherein the selected portion of the body is the head, and the body is in a reclining position, and further comprising head positioning means to support the head between the camera positioning means and the film support means.

15. A portable medical radiographic device for a radiological camera and radiologically sensitive film, comprising:
(a) a mobile base;
(b) an elongate supporting structure attached to the mobile base, the supporting structure comprising a plurality of sections and adjustable joints interconnecting the sections;
(c) means for mounting the radiological camera at a selected position on a first one of the plurality of sections, the means for mounting comprising an elongated arcuate-shaped track for movably mounting the radiological camera on a concave portion thereof, so that rays from the radiological camera are directed away from the concave portion of the track;
(d) means for supporting the radiologically sensitive film at a selected position on a second one of the plurality of sections, the means for supporting comprising an elongated arcuate-shaped cylinder for supporting a film cartridge containing the radiologically sensitive film in a concave portion thereof, so that the radiologically sensitive film is exposed by radiation directed towards the concave portion of the cylinder;
the cylinder fixedly attached to the second one of the plurality of sections and offset therefrom so that, in a plane perpendicular to a longitudinal axis of the second one of the plurality of sections, a first line joining the intersection of the plane with a first point on the cylinder half-way between the longitudinal ends of the cylinder and the intersection of the plane with the longitudinal axis is not perpendicular to a second line tangent to the support at the first point;
(e) energizable camera transport means for moving the radiological camera along the length of the elongated track; and
(f) means for adjustably orienting the position of the track so that the concave portion of the track and the cylinder are positioned in opposition to one another, the first and second ones of the plurality of sections being selected so that when a selected portion of a body is interposed between the camera mounting means and the film support means, the radiological camera and the camera transport means are simultaneously energized, and the concave portions of the track and cylinder are positioned in opposition to one another the moving radiological camera exposes an elongated strip of the radiologically sensitive film, thereby creating a panoramic radiological image of the selected portion of the body.

* * * * *